US007871606B2

(12) United States Patent
Wank

(10) Patent No.: US 7,871,606 B2
(45) Date of Patent: Jan. 18, 2011

(54) USE OF STIMULATED PERIPHERAL-BLOOD MONONUCLEAR CELLS FOR THE TREATMENT OF CANCEROUS DISEASES

(76) Inventor: Rudolf Wank, Hans-Sachs-Strasse 12, Muenchen (DE) 80469

( * ) Notice: Subject to any disclaimer, the term of this patent is extended or adjusted under 35 U.S.C. 154(b) by 1283 days.

(21) Appl. No.: 10/687,913

(22) Filed: Oct. 20, 2003

(65) Prior Publication Data
US 2004/0082065 A1 Apr. 29, 2004

(30) Foreign Application Priority Data
Apr. 26, 2001 (DE) ............... 101 20 505
Apr. 24, 2002 (EP) ............ PCT/EP02/04524

(51) Int. Cl.
*A01N 63/02* (2006.01)
(52) U.S. Cl. ............... 424/93.71; 424/93.21
(58) Field of Classification Search ............. None
See application file for complete search history.

(56) References Cited

U.S. PATENT DOCUMENTS

| 5,217,704 A * | 6/1993 | Johnson et al. ............. 424/1.53 |
| 5,766,920 A * | 6/1998 | Babbitt et al. ............... 435/375 |
| 5,837,233 A * | 11/1998 | Granger .................... 424/93.1 |

FOREIGN PATENT DOCUMENTS

| DE | 68925660 T2 | 6/1989 |
| DE | 19814701 A1 | 4/1998 |
| EP | 409655 A2 * | 1/1991 |
| WO | WO 9520349 A | 1/1995 |
| WO | WO 9520649 A | 8/1995 |
| WO | WO 9629394 A | 9/1996 |
| WO | WO 9732970 A1 * | 9/1997 |
| WO | WO 9950393 A | 10/1999 |

OTHER PUBLICATIONS

Marzo et al., J Immunol. May 15, 1999;162(10):5838-45.*
Gold et al., J Surg Res. Aug. 1995;59(2):279-86.*
RWS Group plc, English language translation of Sep. 12, 2000 of PCT/EP99/02225, filed Mar. 31, 1999.*
Takayama, T. et al., "*Adoptive Immunotherapy to Lower Postsurgical Recurrence Rates of Hepatocellular Carcinoma: A Randomised Trial*," Lancet (2000), vol. 356, n. 9232. pp. 802-807.
Stohl et al., Abstract, "*Stimulation of human peripheral blood mononuclear cells with anti-CD3 monoclonal antibody vs. IL2: disparate effects on T cell-dependent B cell differentiation despite similar effects on generation of unrestricted cytolytic activity*," PubMed 1395122, Clin. Immunol. Immunopathol., (1992), 65(1):30-8.
Baxevauis et al., Abstract, "*Induction of anti-tumor lymphocytes in cancer patients after brief exposure to supernatants from cultures of anti-CD3-stimulated allogeneic lymphocytes*," PubMed 9376269, Br. J. Cancer, (1997) 76(8), pp. 1072-1080.
van Leeuwen et al., "*T cell antigen-receptor signal transduction*," Cuff. Opin. Immunol., (1999), 11:242-248.
Sheehy et al., "*HL-A LD (lymphocyte defined) typing: a rapid assay with primed lymphocytes*," Science, (1975), 188:1308-1310.
Wank et al., "*High risk of squamous cell carcinoma for women with HLA-DQw3*," Nature, (1991), 352:723-725.
Chang, Kenneth J. M.D., et al. "Phase I Clinical Trail of Allogeneic Mixed Lymphocyte Culture (Cytoimplant) Delivered by Endoscopic Ultrasound—Guided Fine-Needle Injection in Patients with Advanced Pancreatic Carcinoma." Cancer Mar. 15, 2000, vol. 88, No. 6. pp. 1325-1335.
Andres Alcover et al., Internalization and Intracelluar Fate of TCR-CD3 Complexes, Critical Reviews in Immunology 20:325-346 (2000).
Haiyan Liu et al., On the Dynamics of TCR:CD3 Complex Cell Surface Expression and Downmodulation, Immunity, vol. 13, 665-675, Nov. 2000.

* cited by examiner

Primary Examiner—Zachary Skelding
(74) Attorney, Agent, or Firm—Crowell & Moring LLP

(57) ABSTRACT

The invention relates to the use of peripheral-blood mononuclear cells that have been stimulated via cascade priming (CAPRI cells) for the purpose of providing an agent for the treatment of cancerous diseases. The CAPRI cells may also be administered in combination with CD3-activated cells.

6 Claims, No Drawings

USE OF STIMULATED PERIPHERAL-BLOOD MONONUCLEAR CELLS FOR THE TREATMENT OF CANCEROUS DISEASES

The invention relates to the use of peripheral-blood mononuclear cells that have been stimulated or activated via "cascade priming" for the purpose of providing an agent for the treatment of cancerous diseases.

The stimulation of naïve (non-stimulated) T-lymphocytes constitutes an important starting-point within the scope of immunotherapy for the purpose of combating cancerous diseases. An optimal activation of naïve T-cells requires a specific antigenic stimulation of the αβ T-cell receptor (TCR) by the MHC peptide/antigen complex (MHC=major histocompatibility complex) in conjunction with co-stimulatory signals. The absence of co-stimulation results in a functional deactivation of the T-cells. The co-stimulatory signals are best provided by the antigen-presenting cells (APC).

The APC are provided with a number of co-stimulatory molecules which contribute substantially to amplifying the specific activation of T-cells via the TCR. Activation-inducing complementary molecules have been able to be identified on T-lymphocytes and APC in the form of membrane proteins. On the T-lymphocytes the membrane proteins are subdivided into T-cell co-receptors, such as the CD4 molecule or the CD8 molecule, and intracellular adhesion molecules-1, 2,3 (ICAM-1,2,3). The latter are expressed by APC and T-cells and enter into reciprocal action with the leucocyte-function antigen-1 (LFA-1 receptor family CD11a/CD18) which is likewise expressed by APC and T-cells. The CD2 molecules, which are expressed by most T-cells, react with CD58 (LFA-3). The T-cells and also the APC express the adhesion molecules LFA-1 and ICAM-1, which are of very great importance for the intensive contact between APC and T-cells. Other molecules having a co-stimulatory function have recently been identified, such as, for example, CD27/CD27L (expand T-cells after CD28 co-stimulation), SLAM (Cdw150, a member of the CD2 family, enhances the production of interferon-γ (IFN-γ) and the proliferation of the memory T-cells) and OX40 (CD134 promotes the response of the type-2 helper T-cells ($T_H2$) and assists the proliferation of $T_H1$ and $T_H2$). The precise function of other co-stimulatory molecules continues to be discussed, but there is no doubt about the importance of elucidation for an understanding of the individual immune response (J. E. M. van Leuwen, L. Samelson, T cell antigen-receptor signal transduction, *Curr. Opin. Immunol.* 11:242-248 (1999)).

Cancer cells provide co-stimulatory signals only to a small extent. Furthermore, cancer cells have a tendency to restrict the expression of MHC molecules drastically and in this way to prevent the recognition of tumour peptides within the MHC context.

Several strategies have been developed in order to counteract the low stimulation of the cancer cells and to imprint the naïve (non-stimulated) T-lymphocytes against the relevant tumour antigens. Many efforts have been made in the direction of improving the co-stimulatory signals with the aid of genetic engineering, for example by transfection of tumour cells with genes that activate T-cells. Furthermore, many efforts have been directed towards the isolation and identification of tumour peptides. Such tumour peptides are used for the loading of APC, in order to enable an efficient presentation of the MHC tumour-peptide complexes to the T-cells. By this means, an activation of the T-cells and the induction of T-cell memory are intended to be obtained. APC that are loaded with antigen are already being re-infused in patients in clinical research centres, in order to attract naïve T-cells and to imprint them against the tumour antigen. Until now, intensive loading of the APC has been undertaken either with tumour peptides/antigens or via an incubation with cancer cells.

The very modest success of these therapeutic strategies is due to four main problems, which may arise individually or in combination: 1) the difficulty in identifying a tumour antigen that induces a strong immune response in each individual; 2) the loss of selected presentation antigens on the tumour cells, which is brought about through the loss of the presentation of individual MHC molecules that presented these tumour antigens/peptides; 3) the capacity of cancer cells to inactivate naïve cells by means of cytokines; and 4) the inadequate occurrence of co-stimulatory signals.

Another strategy for the treatment of, inter alia, cancerous diseases is described in WO 95/20649. A process for producing immune cells generated in vitro is disclosed therein in which peripheral-blood mononuclear cells (PBMC) are incubated with a soluble CD3 antibody, and the supernatant is used for the incubation of naïve PBMC. The immunoreactive cells that are obtained in this way, the T-cell population of which consists predominantly of helper T-cells ($CD4^+$) and cytotoxic T-cells ($CD8^+$), are re-infused in the patients.

Therefore a demand continues to exist for an agent for the treatment of cancerous diseases.

In accordance with the invention, the PBMC that have been stimulated via cascade priming (so-called CAPRI cells) can be employed for the purpose of providing an agent for the treatment of cancerous diseases.

According to the invention, naïve T-cells in the PBMC aggregate of a patient are activated in vitro and imprinted against their own tumour cells; in the process, PBMC come into operation that did not have to be subjected to a previous tumour-antigen loading. For this in-vitro imprinting there is consequently no need to use tumour cells or to identify the specific tumour antigens/peptides.

In the course of cascade priming, naïve PBMC are subjected to primary stimulation by means of agents that stimulate T-lymphocytes, and these PBMC that have been subjected to primary stimulation are added to naïve PBMC, as a result of which the naïve PBMC are stimulated in turn, and the CAPRI cells ("cascade primed" cells) resulting therefrom can be employed, according to the invention, for the purpose of providing an agent for the treatment of cancerous diseases.

The expression "agents that stimulate T-lymphocytes" is to be understood to mean CD3 antibodies, B7 antibodies, lectins, calcium ionophores, allogenic cells, xenogenic cells and the like. The various agents can be employed for primary stimulation on their own or in combination. Primary stimulation is preferably effected via the use of CD3 antibodies, in particular immobilised CD3 antibodies. But stimulation of the naïve PBMC, or rather of the T-lymphocytes in the PBMC aggregate, can also be obtained by means of the other listed measures described in detail in WO 99/50393, which is the property of the applicant and to which reference is expressly made at this point. In the following, the invention will be described in greater detail on the basis of the example of primary stimulation brought about by the CD3 antibodies, without the invention being intended to be restricted thereto.

Primary stimulation of the T-lymphocytes in the PBMC aggregate can be effected by means of CD3 antibodies with subsequent addition of interleukin-2 (IL-2) (so-called IL-2 assistance phase). After an incubation period for the primary stimulation amounting to 4-8 h, naïve PBMC are added to the stimulated PBMC (or rather to the stimulated T-lymphocytes in the PBMC aggregate). After a further incubation period of at least 18-24 h (so-called imprinting phase), the stimulation of the naïve PBMC is concluded, so that the preparation of cells with addition of IL-2 can be expanded for about 3 days and/or employed in accordance with the invention (so-called expansion phase). During this further incubation, a continuous further stimulation of the cells that have already been subjected to primary stimulation takes place, whereas the newly added naïve PBMC are mainly stimulated via the cells that were subjected to primary stimulation in the first step. The numerical ratio of the PBMC subjected to primary stimulation to the naïve PBMC amounts, as a rule, to about 1:1. The process for producing CAPRI cells and the use thereof for the treatment of diseases, disorders and defects associated with the brain have already been addressed in WO 99/50393, which is the property of the applicant.

According to another embodiment, during the IL2 assistance phase and/or during the imprinting phase other cytokines, such as, for example, IL-4 and/or GMCSF ("IL-4 CAPRI cells") or interferons ("IFN-γ CAPRI cells"), may be added, in order in this way to obtain the expression of other peptides by the APC and to promote the expansion of other APC or T-cell subpopulations. The CAPRI cells may be employed in a new round of imprinting of naïve cells, with subsequent expansion.

According to another embodiment, the ratio of the co-cultivated activated PBMC to the naïve PBMC can be changed from 1:1 to 1:10 or 10:1, i.e. a hundred fold.

According to another embodiment, allogenic (foreign) immune cells can also be employed in the production of CAPRI cells. In related individuals, in whom one or two HLA haplotypes (HLA=human major histocompatibility complex) coincide, a sufficient immune-cell cooperation between the naïve T-cells and the activated APC can be guaranteed. In the case of a different haplotype, an additional stimulation may occur (allo-stimulation). The allo-stimulation of a haplotype difference was described quite some time ago (M. J. Sheehy, P. M. Sondel, M. L. Bach, R. Wank, F. H. Bach, HL-A LD (lymphocyte defined) typing: a rapid assay with primed lymphocytes, *Science* 188:1308-1310 (1975)). Cells of non-related individuals can also be used if sufficient HLA coincidence for an HLA-restricted lysis exists between the allogenic cells and the tumour cells of the patient. The following combinations can be employed advantageously in the treatment of cancerous diseases:

1) Activated APC of the patient+naïve PBMC of an individual who exhibits the same relevant HLA alleles: the memory effector cells that are generated do not come from the patient and are consequently allo-CAPRI cells. This constitutes the most frequent variant, since in most cases the APC of the patient best present the tumour peptides.
2) APC from a "resistant" individual (e.g. resistant to the human papilloma virus, HPV, R. Wank, C. Thomssen, High risk of squamous cell carcinoma of the cervix for women with HLA-DQw3, *Nature* 352:723-725 (1991)) are used for the purpose of imprinting naïve PBMC of a patient with cervical cancer induced by HPV: the APC are foreign (allo), the memory effector cells that are generated come from the patient and are consequently allo-APC-CAPRI.
3) The APC and also the memory effector cells that are generated are foreign (allo) and are consequently allo-allo-CAPRI cells. The allo-allo-CAPRI cells are optimal if both the patient and the allogenic donor have come into contact with the same carcinogenic factor and the allogenic donor displayed a superior immune response.

The kinetics of the allogenic or semi-allogenic CAPRI combinations do not differ from those of the "normal" CAPRI method.

In another preferred embodiment of the invention, CAPRI cells are administered in combination with CD3-activated cells or with CD3-activated cells that had been polarised in the direction of the $T_H1$ population by addition of IFN-γ or in the direction of the $T_H2$ and $CD8^+$ T-cell populations by addition of IL-4.

In part this has historical reasons, since prior to the invention of CAPRI cells only the CD3-activated cells were employed in the case of other indications. As the treatment with only CD3-activated cells has an advantageous effect with respect to a low rate of tumour recurrence (T. Takayama et al., Adoptive immunotherapy to lower postsurgical recurrence rates of hepatocellular carcinoma: a randomised trial, *Lancet* 356:802-807 (2000)), possibly by reason of the increased number of $CD8^+$ T-cells, these cells can be administered for the purpose of assisting the CAPRI cells. In addition, CD3-activated cells can be employed successfully in patients with depressive disorders, as already described in DE 198 14 701, which is the property of the applicant. These effects can also be exploited successfully in combating the negative consequences of chemotherapy or irradiation.

Without there being any intention to be tied down to a particular theory for explaining the ascertainable effect of the CAPRI cells for the purpose of combating tumour cells, the active mechanism, which is elucidated in greater detail in the following, will be considered.

In the course of stimulation via cascade priming it is assumed that the induction of the immune response is begun by a general activation of the naïve T-cells in the PBMC aggregate (by means of CD3 antibodies). These activated T-cells secrete a number of cytokines which activate the APC (monocytes/macrophages, dendritic cells, B-lymphocytes). Correspondingly, activated APC secrete a large number of cytokines and express co-stimulatory ligands to an increased extent. Still more significant, however, is the more efficient presentation of peptides of endogenous or exogenous origin by the APC. In the case of such peptides it may be a question of tumour peptides that are generated by cancer cells and that are now presented by the APC to an increased extent. It is assumed that stimulation of the naïve cells that are subsequently added is effected quite predominantly by the activated APC of the PBMC that have been subjected to primary stimulation, i.e. in highly specific manner via the αβ TCR of the T-lymphocytes ($CD4^+$ helper cells and $CD8^+$ killer cells) in the naïve PBMC population.

The various phases that are passed through during cascade priming will be examined in still more detail in the following.
1) T-cell activation via CD3-induction of the secretion of cytokines
   The binding of T-lymphocytes to immobilised CD3 antibodies and the addition of IL-2 result in an activation of the T-lymphocytes via the invariant CD3 polypeptides which are associated with the αβ TCR. The activation also induces a secretion of cytokines by the T-cells. In this phase the type of the T-cell population can be influenced and expanded by addition of cytokines; for instance, by addition of IL-4 a subsequent amplification can be steered in the direction of the $T_H2$ cells. In this phase a significant proliferation of the $CD8^+$ T-cells can also be observed.
2) Activation of the APC
   The cytokines of the T-cells activate the APC, monocytes differentiate into macrophages, and dendritic cells mature. The cytokines that are produced by the variously activated T-cells influence the prevailing type of the APC and also influence the type of the enzymatic subunits which are activated in the APC. Correspondingly, the activated APC secrete cytokines which assist the activation of the naïve cells in the imprinting phase.

3) Imprinting phase: expression of MHC peptide complex and of co-stimulatory molecules by the APC Activated APC secrete cytokines, express co-stimulatory molecules and the MHC peptide complex, either de novo and/or in higher concentrations. Naïve PBMC are now added to the activated PBMC in equal parts. Activated APC express, for example, the co-stimulatory B7 molecules CD80/CD86, adhesion molecules and other co-stimulatory molecules together with the MHC peptide complex, resulting in a complete activation of the T-cells via the $\alpha\beta$ TCR in effector T-cells and memory T-cells. Some monocytes from the freshly added naïve PBMC differentiate, by virtue of the cytokines that are produced and/or by virtue of the contact with activated T-cells as in 1) or 2), to form dendritic cells. It is conceivable that dendritic cells not only induce the memory of the T-cells but also refresh the memory of the T-cells in the in-vivo situation by presentation of the MHC peptide complexes.

The advantage of the use, according to the invention, of cascade priming in connection with the provision of an agent for the treatment of cancerous diseases in comparison with all the previously known activation methods lies in its specificity and in the speed of the induction of memory in the lymphocytes. The cascade priming requires only 24 h until the full cytotoxic capacity of the T-cells in the PBMC aggregate is obtained, without it being necessary for the tumour peptides/antigens to be known.

In explaining the clearly increased efficacy of CAPRI cells in comparison with only CD3-activated T-cells in the PBMC aggregate, it is assumed, inter alia, that, depending on the method of activation, a different weighting of the various immune-cell subpopulations arises. For instance, with the aid of a FACS analysis (fluorescence-activated cell sorter), quantitative differences in the occurrence of the $CD4^+$ T-cells (helper cells) and of the $CD8^+$ T-cells (cytotoxic cells) and also of the $CD45RO^+$ T-cells (memory T-cells) can be ascertained. CD3-activation of the PBMC results in approximately 25% $CD4^+$ T-cells and 58% $CD8^+$ T-cells; the converse was observed in the case of memory imprinting, which resulted in 54% $CD4^+$ T-cells and 29% $CD8^+$ T-cells. The most significant feature in this case is the rise in the $CD45RO^+$ memory cells in the course of cascade priming. Only 3% of the unstimulated (naïve) PBMC show a $CD45RO^+$ phenotype; 29% of the CD3-stimulated cells; and 49% of the CAPRI cells. This increase in memory cells in the course of cascade priming is of great importance in connection with combating tumour cells, since memory effector cells require no co-stimulation, or only very low co-stimulation, for their cytotoxic activity. A further characteristic of memory effector cells is their capacity for MHC-restricted lysis.

For instance, CAPRI cells are capable of lysing allogenic cancer-cell lines, i.e. cancer-cell lines of other, foreign patients, in highly specific manner, or rather in MHC-restricted manner, on condition that the allogenic cancer-cell lines and the cytotoxic CAPRI cells exhibit a common MHC antigen.

As already explained, memory effector cells can be obtained against unidentified peptides of unknown infections with the aid of cascade priming. The precise function of such unknown, or sometimes even known, chronic infections in carcinogenesis is the object of intense research. Many viruses are known to be principal factors in carcinogenesis, such as, for example, the human papilloma viruses (HPV) 16/18 in cervical carcinomas. Other viruses are under similar suspicion, even if no immunogenic peptides have yet been able to be identified. An example is the JC virus, which appears to be an important carcinogenic factor in colorectal carcinomas. Although a regression of colorectal carcinomas in patients has been able to be obtained by administration of CAPRI cells, it remains unclear whether the JC-viral peptides or other peptides of the tumour cells constitute the actual targets of attack of the lytic activity of the CAPRI cells.

CAPRI cells can be employed in a dosage quantity of 0.5-30 million cells per injection. The quantity of injected cells can be adapted, depending on the age, body weight and/or possible secondary diseases of the patient. It is possible to increase—or, where appropriate, to decrease—the injected cell quantity with increasing duration of treatment. As a rule, the cell quantity per injection in adult patients is about 1-20 million cells per injection.

The injections can be administered at different time-intervals, such as once to several times a week, every couple of weeks, or at still longer time-intervals.

The injections of CAPRI cells are administered intradermally, intravenously and/or intramuscularly. If the size of the tumour does not exceed a diameter of 0.5 cm, the CAPRI cells can be administered into the tumour instead of around the tumour. Administration is preferably effected via a combined intradermal and intravenous injection.

According to a preferred embodiment, CD3-activated cells in a dosage within the range of 1-15 million cells are administered to the patients in addition to the CAPRI cells. The CD3-activated cells may be administered either into a different place in the body than the CAPRI cells or into the vicinity of the intradermal CAPRI infiltration site. Administration is preferably effected via an intradermal and/or intramuscular injection.

Treatment of cancerous diseases by the use, according to the invention, of CAPRI cells may also be undertaken in addition to therapy of a different kind. For instance, CAPRI cells, where appropriate in combination with CD3-activated cells, can be employed for the purpose of providing an agent for the treatment of cancerous diseases in addition to conventional medicaments which are administered within the scope of chemotherapy. Furthermore, these cells may be administered in addition to radiotherapy.

EXAMPLES

1. Methods for Producing CAPRI Cells

1) Start of the CD3-Activation Phase (2-4 h):

10-20 million PBMC (segregated via a Ficoll-Hypaque gradient) are suspended in a volume of 10-12 ml culture medium (such as, for example, RPMI1640), supplemented with 10% HyClone foetal calf serum, and deposited onto immobilised anti-CD3 monoclonal antibodies. The HyClone serum may be replaced at any time by autologous serum.

2) IL2 Assistance Phase (2-3 h):

After 2-4 h of CD3 activation, 20 units IL-2/ml are added for the purpose of assisting the activation and preventing apoptosis.

3) Imprinting Phase (18-24 h):

After 2-3 h of TL2 assistance, the APC are sufficiently activated for an imprinting of naïve PBMC: 10-20 million naïve PBMC in a supplemented culture medium are added to the stimulated PBMC.

4) Expansion Phase (72 h, Optional):

The imprinted PBMC (now CAPRI cells) are counted and resuspended in a supplemented medium with 20 units IL-2/ml at a concentration of approximately 0.2-0.4 million cells/ml.

5) Harvesting of CAPRI Cells:

After 72 h of expansion, the cells are harvested and stored, frozen in aliquots of 2-30 million/ampoule, or employed immediately within the scope of a treatment.

The use of allogenic cells in the various steps of cascade priming, and also other modifications, can be implemented without changing the basic process.

The production of CAPRI cells and of CD3-activated cells is described in detail in WO 99/50393, which is the property of the applicant.

2. Procedure for the Therapeutic Administration of CAPRI Cells

The CAPRI cells are resuspended in a small volume (1 ml) of PBS (phosphate-buffered salt solution) and preferably injected intradermally and intravenously. They may also be injected intramuscularly or may be infiltrated around the tumour, in addition into the tumour if the size of the tumour does not exceed a diameter of 0.5 cm. Depending on the indication, the procedure is begun with aliquots of approximately 0.5 million CAPRI cells, but no more than 30 million cells should be administered per injection. If, in addition, CD3-activated cells are being administered, injection is effected in a dosage of 1-20 million cells. Administration is effected via an intradermal and/or intramuscular injection.

3. In-Vitro Studies of the Activity of CAPRI Cells

A) Solid cancer-cell lines were lysed within 24 h by CAPRI cells. It became evident that CAPRI cells can be employed again after destroying a cancer-cell line. CAPRI cells were able to be applied up to 7 times onto another cancer-cell line and were able to destroy the latter with the same efficiency. In this connection no cytokines had to be employed for the purpose of assisting the CAPRI cells. The cancer-cell lines that were tested originated from a melanoma (one line), carcinoma of the breast (nine lines), colon carcinoma (three lines), glioblastoma multiforme (two lines) and bowenoid papilloma (one line). Particularly in the case of the bowenoid tumour, the superiority of CAPRI cells (i.e. naïve PBMC imprinted with activated PBMC of the patient) in comparison with PBMC cells that had been activated and imprinted in the presence of a bowenoid tumour-cell line became evident. The former were capable of lysis; the latter, in contrast, were not. The composition of this bowenoid tumour-cell line is of particular interest in this connection, since this tumour-cell line consisted of only approximately 3% tumour cells, the remaining 97% being fibroblasts. The capacity of the CAPRI cells to discover the cancer cells "behind" the fibroblasts is of the greatest importance, above all, in connection with metastatic lesions which are quite frequently surrounded by fibroblast layers. In contrast with the CAPRI cells, the cells that were only CD3-activated were not capable of destroying the solid cancer-cell lines enumerated above. It must be pointed out that in the case of fresh single-cell suspensions of tumour biopsies or cancer-cell lines it has already been possible to show repeatedly that the latter are susceptible to lysis by CD3-activated cells. But in the case of these tumour cells it was a question of single-cell suspensions that had been previously damaged by enzymatic treatment and that did not have the opportunity to regenerate and to build up a solid tumour line.

B) In association studies with nine breast-carcinoma cell lines that originated from fresh tumour biopsies, an MHC-Class-II-restricted lysis became evident. For instance, CAPRI cells from a donor with HLA Class II allele DQB1*0201 lysed the autologous cancer-cell line (also with HLA-DQB1*0201) and other, allogenic breast-cancer cell lines which likewise were positive for DQB1*0201. The same occurred in the case of CAPRI cells that were HLA-DQB1*0603-restricted. Only the HLA-DQB1*0603-positive autologous cancer-cell lines and other cancer-cell lines of type HLA-DQB1*0603 were lysed. Even though the HLA-Class-II-restricted lysis was dominant in the case of carcinoma of the breast, an HLA-Class-I-restricted lysis was nevertheless observed in one case. Antibodies against the presenting HLA Class II molecules blocked the lysis of cancer cells completely, whereas antibodies against the HLA Class I molecules only slightly reduced the lysis of cancer cells. The removal of $CD4^+$ or $CD8^+$ immune cells after cascade priming via a magnetic bead separation, however, resulted in complete loss of lytic activity of the CAPRI cells that were left behind. In contrast, the removal of $CD56^+$ or $CD57^+$ natural killer cells had practically no influence on lytic activity. This points to the conclusion that CAPRI cells also perform HLA-Class-I-restricted lysis, predominantly however HLA-Class-II-restricted lysis. Natural killer cells, which are positive for CD4 or CD8 but negative for CD56 or CD57, possibly contribute—to a small extent—to the lytic activity of the CAPRI cells.

4. In-Vivo Studies

A) The in-vivo efficacy of the CAPRI cells was able to be ascertained on the basis of an examination of accessible tumours. The following tumours were treated and examined: one melanoma, cutaneous metastases of two patients with breast cancer, cutaneous metastases of one patient with ovarian cancer and one bowenoid papilloma. The method of application was a direct injection into and around the tumour, if the tumour was no larger than 0.5 cm in diameter. In larger tumours, for example in the case of a cutaneous metastasis measuring 5 cm×8 cm of the patient with ovarian cancer, the injection was placed at the edge of the tumour—that is to say, in the expansion region. All the tumours that were treated in this way showed a rapid regression after 6-8 weeks with weekly or twice-weekly injection. This result is of interest, above all, in the case of the patient with the bowenoid papilloma, since this patient had been treated five times within one year in the dermatological hospital of Munich University by laser surgery and by local application of creams. Nevertheless, prior to the injection of CAPRI cells the tumour cells kept reappearing in the vulvar and anal regions. The patient has now been free of tumours for two years.

B) Within the scope of the study of the in-vivo efficacy of CAPRI cells, a breast-cancer patient was treated who exhibited five hepatic metastases which had been detected both by biopsies and by ultrasound and CT. Two injections per week of at least 20 million, but no more than 30 million, CAPRI cells were administered intravenously to this patient, who underwent no other treatment during the period of the CAPRI-cell treatment. Initial unmistakable symptoms of a regression of the tumour were able to be ascertained after 8 weeks by ultrasonic examinations. In four out of four patients with a metastatic colon carcinoma the treatment with CAPRI cells induced a significant regression of the tumour. Two of these four patients were no longer receiving any chemotherapy, by reason of the considerable side-effects and/or by reason of lack of effectiveness.

C) In the case of the patients described under A) and B), either no further medication was administered or the previous medication was not changed. In addition to the CAPRI cells, CD3-activated cells were also employed.

D) The effects, described above, of the CAPRI cells were obtained in autologous systems. However, allogenic (foreign) cells in various stages of cascade priming may also be employed. This has only been carried out in a few patients who had lost the majority of their immune cells during chemotherapy. Allogenic cells can sometimes intensify the lytic activity of the CAPRI cells. It is possible, for example, to employ the cells of the patient for the first step of the activation (see "Methods for producing CAPRI cells", steps 1 and 2) and then to use allogenic naïve PBMC for an imprinting with the autologous activated PBMC of the patient (allo-CAPRI). In one family with a patient with a colorectal carcinoma, whose father had not developed any cancerous disease but in whom, however, polyps in the colon were repeatedly appearing, a phenomenon which, as is known, may be appraised as an early stage of cancer, the APC of the father (allo-APC) were able to be used for the purpose of imprinting the naïve immune cells of the patient. In this case the paternal APC were able to imprint the naïve PBMC of the patient and in this way to result in the formation of memory effector cells, a result which was able to be tested on the basis of the cancer-cell line of the patient. In this special family situation, allo-allo-CAPRI cells were also able to be induced, that is to say, the activated APC of the father were able to imprint the naïve PBMC of the father, and the cells obtained in this way were capable of lysing the cancer-cell line of the patient (the son). It must be pointed out that these paternal CAPRI cells, which were used as allo-allo-CAPRI cells on the cancer-cell lines of the patient, had no contact at all with the cells of the patient, neither with the APC nor with the cancer cells of the patient, and not even with peptides that had been eluted from such cancer cells.

The invention claimed is:

1. A method for treating cancer, the method comprising:
   (a) stimulating peripheral-blood mononuclear cells (PBMC) with immobilized anti-CD3 antibodies to produce primary stimulated PBMC;
   (b) adding naïve PBMC to the primary stimulated PBMC;
   (c) incubating the naïve PBMC added in step (b) in the presence of the primary stimulated PBMC produced in step (a) to stimulate the naïve PBMC by the primary stimulated PBMC, thereby obtaining PBMC that have been stimulated via cascade priming of steps (a) to (c) (CAPRI cells); and;
   (d) administering the CAPRI cells into a cancer patient,
   wherein the primary stimulation of step (a) and/or the stimulation of naïve PBMC of step (c) occurs in the presence of at least one cytokine selected from the group of interleukin-2 (IL-2), interleukin-4 (IL-4), and interferon γ (IFN-γ).

2. The method of claim 1, wherein the cancer is selected from the group consisting of melanoma, breast carcinoma, colorectal carcinoma, ovarian carcinoma, glioblastoma multiform, and bowenoid papilloma.

3. The method of claim 1, wherein administering the CAPRI cells comprises:
   injecting CAPRI cells intradermally, intravenously, and/or intramuscularly.

4. The method of claim 1, wherein administering the CAPRI cells comprises:
   injecting CAPRI cells in a dosage range from 0.5 to 30 million cells per injection into the cancer patient.

5. The method of claim 1, wherein administering the CAPRI cells comprises:
   administering CAPRI cells into a tumor of the cancer patient, wherein the diameter of the tumor is less than 0.5 cm.

6. The method of claim 1, wherein the CAPRI cells are administered in conjunction with radiotherapy.

* * * * *

UNITED STATES PATENT AND TRADEMARK OFFICE
CERTIFICATE OF CORRECTION

PATENT NO. : 7,871,606 B2
APPLICATION NO. : 10/687913
DATED : January 18, 2011
INVENTOR(S) : Rudolf Wank Page 1 of 1

It is certified that error appears in the above-identified patent and that said Letters Patent is hereby corrected as shown below:

Title Page:

Insert --(63) Related U.S. Application Data: This application is a continuation of PCT/EP02/04524, filed on April 24, 2002.--

(30) Foreign Application Priority Data should read:
April 26, 2001 (DE) 101 20 505

Signed and Sealed this
Sixth Day of November, 2012

David J. Kappos
*Director of the United States Patent and Trademark Office*